(12) United States Patent
Choe

(10) Patent No.: US 12,274,558 B2
(45) Date of Patent: Apr. 15, 2025

(54) DEVICE, METHOD AND COMPUTER PROGRAM FOR ANALYSIS OF SLEEP TIME USING RADAR

(71) Applicant: BITSENSING INC., Seongnam-si (KR)

(72) Inventor: Sun Taag Choe, Seoul (KR)

(73) Assignee: BITSENSING INC., Seongnam-si (KR)

( * ) Notice: Subject to any disclaimer, the term of this patent is extended or adjusted under 35 U.S.C. 154(b) by 98 days.

(21) Appl. No.: 18/119,529

(22) Filed: Mar. 9, 2023

(65) Prior Publication Data

US 2023/0284970 A1 Sep. 14, 2023

(30) Foreign Application Priority Data

Mar. 10, 2022 (KR) .................. 10-2022-0030088
Feb. 23, 2023 (KR) .................. 10-2023-0024056

(51) Int. Cl.
*A61B 5/00* (2006.01)
*A61B 5/24* (2021.01)

(52) U.S. Cl.
CPC .............. *A61B 5/4812* (2013.01); *A61B 5/24* (2021.01); *A61B 5/4815* (2013.01)

(58) Field of Classification Search
CPC ............ B60W 30/06; B60W 60/0011; B60W 50/0098
See application file for complete search history.

(56) References Cited

U.S. PATENT DOCUMENTS

2020/0178892 A1* 6/2020 Maslik ................. A61B 5/4836
2022/0047208 A1* 2/2022 Shin ......................... A61B 5/11

FOREIGN PATENT DOCUMENTS

KR 1020140087902 A 7/2014
WO 2016170005 A1 10/2016

OTHER PUBLICATIONS

Extended European Search Report for EP application No. 23161123.7 dated Jul. 19, 2023.

* cited by examiner

*Primary Examiner* — Quan Zhen Wang
*Assistant Examiner* — Mancil Littlejohn, Jr.
(74) *Attorney, Agent, or Firm* — Dinsmore & Shohl LLP; Yongsok Choi, Esq.

(57) ABSTRACT

A device for analysis of sleep time using a radar includes a transceiver configured to transmit a radar signal toward a subject and receive the radar signal reflected from the subject; a breathing signal collection unit configured to collect a breathing signal of the subject based on the radar signal; a first sleep time detection unit configured to detect a first sleep time of the subject from the breathing signal based on a presence discriminator; a second sleep time detection unit configured to detect a second sleep time of the subject based on a probability value of the first sleep time; and a final sleep time determination unit configured to determine a final sleep time of the subject based on the second sleep time.

14 Claims, 13 Drawing Sheets

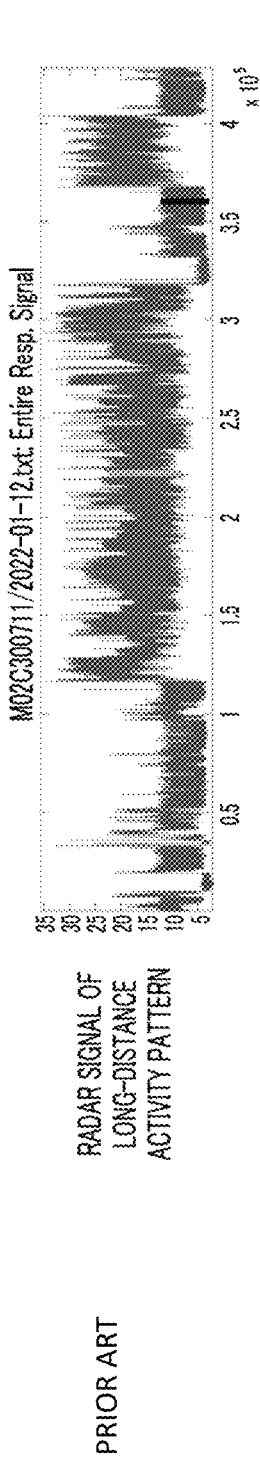
FIG. 1A(i)
RADAR SIGNAL OF LONG-DISTANCE ACTIVITY PATTERN
PRIOR ART
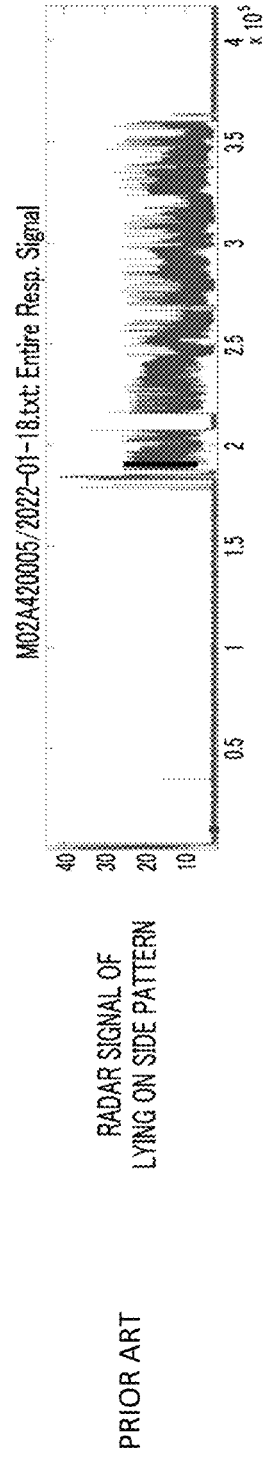
FIG. 1A(ii)
RADAR SIGNAL OF LYING ON SIDE PATTERN
PRIOR ART
FIG. 1A(iii)
RADAR SIGNAL OF MISDETECTION OBJECT PATTERN
PRIOR ART

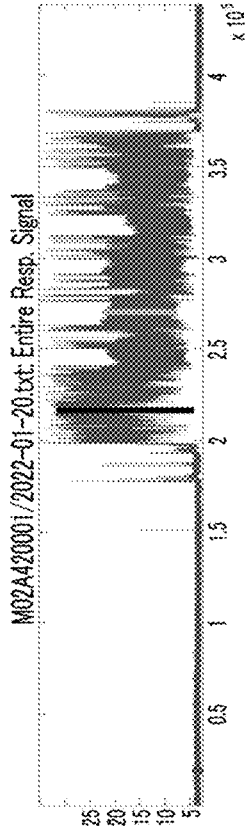
FIG. 1A(iv)
RADAR SIGNAL OF STABLE STANDARD PATTERN
PRIOR ART
FIG. 1B(i)
RADAR SIGNAL OF LONG-DISTANCE ACTIVITY PATTERN
PRIOR ART
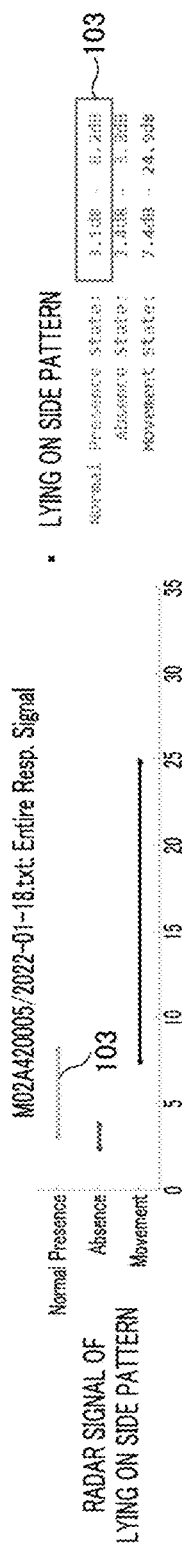
FIG. 1B(ii)
RADAR SIGNAL OF LYING ON SIDE PATTERN
PRIOR ART

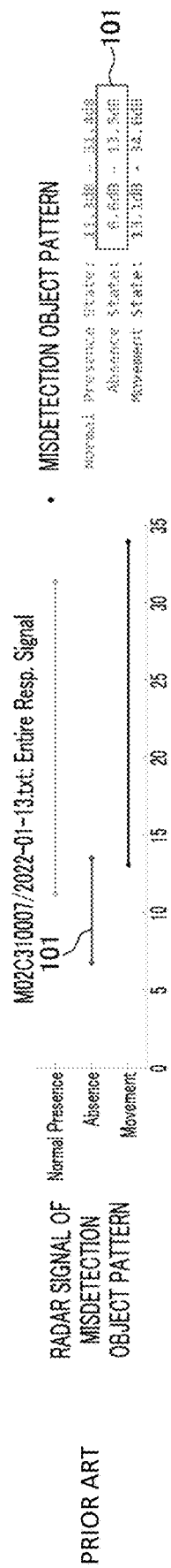
FIG. 1B(iii)
PRIOR ART
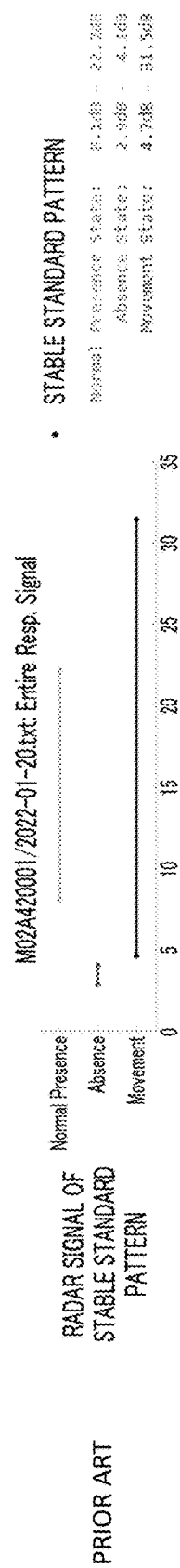
FIG. 1B(iv)
PRIOR ART

413
<SECOND SLEEP TIME>

415
<RESULT OF ANALYSIS ON SLEEP CONTINUITY>

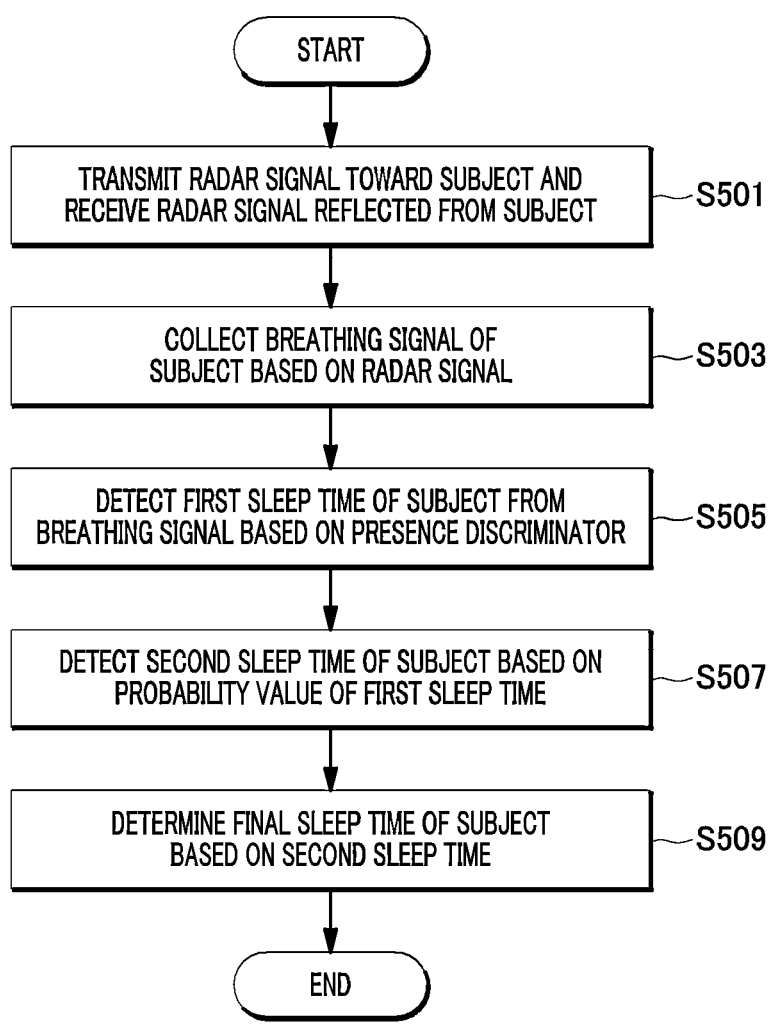

DEVICE, METHOD AND COMPUTER PROGRAM FOR ANALYSIS OF SLEEP TIME USING RADAR

CROSS-REFERENCE TO RELATED APPLICATION

This application claims the benefit under 35 USC 119(a) of Korean Patent Applications No. 10-2022-0030088 filed on Mar. 10, 2022, and No. 10-2023-0024056 filed on Feb. 23, 2023 in the Korean Intellectual Property Office, the entire disclosures of which are incorporated herein by reference for all purposes.

TECHNICAL FIELD

The present disclosure relates to a device, a method and a computer program for analysis of sleep time using a radar.

BACKGROUND

Polysomnography is a test used to measure the quality and amount of sleep and detect sleep diseases and sleep-related disorders. In general, polysomnography is used to detect a variety of sleep diseases and sleep disorders by measuring physiological and physical signals from human body during sleep. For example, brain waves, electrooculogram, electromyogram, electrocardiogram, arterial blood, oxygen saturation, abdominal and thoracic breathing exercises, respiratory air flow, snoring and body postures are measured.

A basic method for measuring sleep time uses a wearable deice (e.g., wrist actigraphy device) to measure a sleep time of a wearer based on activities (e.g., the amount of activity based on wrist movements) of the wearer.

However, the conventional wearable device-based sleep test method needs to be performed while a tester is worn on a part of a human body, and depends only on an expensive tester to more precisely examine sleep diseases.

Meanwhile, according to a radar-based sleep estimation method, a radar sensor transmits a radar signal toward a human subject, receives the radar signal reflected from the human subject and measures sleep time based on the received radar signal.

The radar-based sleep estimation method does not require attachment of a tester to a human subject and thus does not shackle the human subject, and causes less First Night Effect (FNE) that may interfere with sleep analysis of the human subject and thus facilitates sleep analysis.

However, the radar signal contains information about a broad area and thus may contain a misdetection object which can be mistaken for the human subject.

A radar device can filter a fixed object by signal processing, but cannot filter movements of an object that generates micro-vibrations such as breathing of the human subject. Herein, examples of the movements of the object that generates micro-vibrations may include a case where a curtain containing a metallic material sways in the wind, a case where a plant having a high water content sways in the wind, and a case where metallic curtain rings that transmit radio waves sway in the wind.

FIG. 1A and FIG. 1B are diagrams provided to explain problems of radar signals used for conventional sleep analysis.

FIG. 1A shows radar signal patterns depending on a plurality of set-up environment patterns. Referring to FIG. 1A(i), a long-distance activity pattern is a radar signal pattern of a sleep testee measured in a multi-person room of a sanatorium. In the multi-person room of the sanatorium, a bed is used only for rest or sleep and other users may reside around the bed. Also, it can be seen that when the sleep testee is present at a short distance from a radar sensor in the room, the strength of movement of the sleep testee (i.e., intensity of radar signals) is measured high and when the sleep testee is present at a long distance form the radar sensor, the strength of movement of the sleep testee is measured relatively low.

Referring to FIG. 1A(ii), a lying on side pattern is a signal pattern generated when a sleep testee in a single person home environment sleeps while lying on his/her side. Referring to the lying on side pattern, a breathing waveform of the sleep testee is apparently observed and the intensity of radar signal is measured very low.

Referring to FIG. 1A(iii), a misdetection object pattern is a radar signal pattern of a misdetection object measured in a multi-person room of a sanatorium. The misdetection object pattern does not contain a breathing pattern, but contains an irregular noise pattern. It can be presumed from the misdetection object pattern that an object such as a large size curtain or small metallic ring around a sleep testee keeps swaying in the wind.

Referring to FIG. 1A(iv), a stable standard pattern is a signal pattern generated when there is no misdetection object around a bed in a single person home environment and a sleep testee sleeps while maintaining a supine position. Referring to the stable standard pattern, it can be seen that noises generated when the sleep testee moves, stops and is absent can be clearly distinguished.

FIG. 1B shows a signal intensity of a normal presence state, a signal intensity of an absence state and a signal intensity of a movement state measured from respective radar signals depending on the plurality of set-up environment patterns of FIG. 1A.

Referring to FIG. 1B, a signal intensity 101 of the absence state in the misdetection object pattern is higher than a signal intensity 103 of the normal presence state in the lying on side pattern and a signal intensity 105 of the movement state in the long-distance activity pattern. Therefore, comparison of intensity of measured signals is not enough to confirm the presence or absence of the sleep testee.

PRIOR ART DOCUMENT (Patent Document 1) Korean Patent Laid-open Publication No. 10-2014-0087902 (published on Jul. 9, 2014)

SUMMARY

In view of the foregoing, the present disclosure is provided to collect sleep-related breathing signals of a subject by using a radar and analyze a sleep time of the subject based on the breathing signals of the subject by using a presence discriminator.

The problems to be solved by the present disclosure are not limited to the above-described problems. There may be other problems to be solved by the present disclosure.

According to an exemplary embodiment, a device for analysis of sleep time using a radar may include a transceiver configured to transmit a radar signal toward a subject and receive the radar signal reflected from the subject; a breathing signal collection unit configured to collect a breathing signal of the subject based on the radar signal; a first sleep time detection unit configured to detect a first sleep time of the subject from the breathing signal based on a presence discriminator; a second sleep time detection unit configured to detect a second sleep time of the subject based on a probability value of the first sleep time; and a final sleep time determination unit configured to determine a final sleep time of the subject based on the second sleep time.

According to another exemplary embodiment, a method for analysis of sleep time using a radar that is performed by a sleep time analysis device may include transmitting a radar signal toward a subject and receiving the radar signal reflected from the subject; collecting a breathing signal of the subject based on the radar signal; detecting a first sleep time of the subject from the breathing signal based on a presence discriminator; detecting a second sleep time of the subject based on a probability value of the first sleep time; and determining a final sleep time of the subject based on the second sleep time.

According to another exemplary embodiment, a non-transitory computer-readable storage medium that stores a sequence of instructions for analysis of sleep time using a radar, wherein the sequence of instructions, when executed by a computing device, causes a computing device to: transmit a radar signal toward a subject and receive the radar signal reflected from the subject, collect a breathing signal of the subject based on the radar signal, detect a first sleep time of the subject from the breathing signal based on a presence discriminator, detect a second sleep time of the subject based on a probability value of the first sleep time, and determine a final sleep time of the subject based on the second sleep time.

This summary is provided by way of illustration only and should not be construed as limiting in any manner. Besides the above-described exemplary embodiments, there may be additional exemplary embodiments that become apparent by reference to the drawings and the detailed description that follows.

According to any one of the above-described embodiments of the present disclosure, it is possible to collect sleep-related breathing signals of a subject by using a radar and analyze a sleep time of the subject based on the breathing signals of the subject by using a presence discriminator.

Also, according to the present disclosure, it is possible to determine whether or not the subject is present by using the presence discriminator unlike a conventional case where it is impossible to determine whether or not the subject is present based on the intensities of radar signals.

Further, according to the present disclosure, sleep breathing signals can be easily collected in everyday life by using the radar. Thus, it is possible to easily analyze a sleep time of the subject in a contactless manner.

Furthermore, according to the present disclosure, the radar is used to analyze sleep-related breathing signals of the subject. Thus, it is possible to reduce inconveniences associated with conventional polysomnography.

BRIEF DESCRIPTION OF THE DRAWINGS

In the detailed description that follows, embodiments are described as illustrations only since various changes and modifications will become apparent to a person with ordinary skill in the art from the following detailed description. The use of the same reference numbers in different figures indicates similar or identical items.

FIG. 1A(i) through 1A(iv) and FIG. 1B(i) through 1B(iv) are diagrams provided to explain problems of radar signals used for conventional sleep analysis.

FIG. 5 is a flowchart showing a method for analyzing sleep time using a radar according to an embodiment of the present disclosure.

DETAILED DESCRIPTION

Figure 2A:
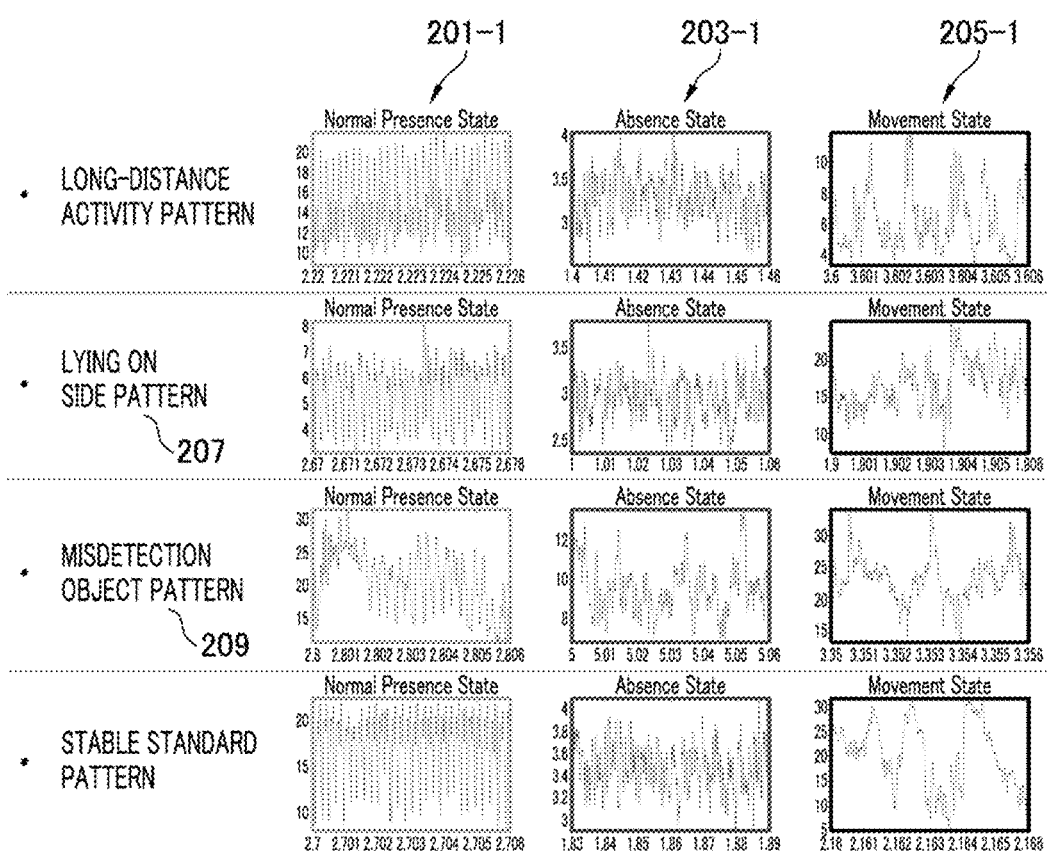
FIG. 2A to FIG. 2D are diagrams provided to explain a method for calculating a normalized discriminator to be used for a presence discriminator according to an embodiment of the present disclosure.

Hereafter, example embodiments will be described in detail with reference to the accompanying drawings so that the present disclosure may be readily implemented by those skilled in the art. However, it is to be noted that the present disclosure is not limited to the example embodiments but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected" another element and an element being "electronically connected" to another element via another element. Further, it is to be understood that the terms "comprises," "includes," "comprising," and/or "including" means that one or more other components, steps, operations, and/or elements are not excluded from the described and recited systems, devices, apparatuses, and methods unless context dictates otherwise; and is not intended to preclude the possibility that one or more other components, steps, operations, parts, or combinations thereof may exist or may be added. Throughout this document, when a member is said to be located "on" another member, this includes not only when the member is in contact with another member, but also when other member is present between the two members.

Throughout this document, the term "unit" may refer to a unit implemented by hardware, software, and/or a combination thereof. As examples only, one unit may be implemented by two or more pieces of hardware or two or more units may be implemented by one piece of hardware.

Throughout this document, a part of an operation or function described as being carried out by a terminal or device may be implemented or executed by a device connected to the terminal or device. Likewise, a part of an operation or function described as being implemented or executed by a device may be so implemented or executed by a terminal or device connected to the device.

Hereafter, embodiments of the present disclosure will be described in detail with reference to the accompanying configuration views or process flowcharts.

FIG. 2A to FIG. 2D are diagrams provided to explain a method for calculating a normalized discriminator to be used for a presence discriminator according to an embodiment of the present disclosure.

FIG. 2A shows graphs of breathing waveforms of a sleep testee, and enlarges a radar signal 201-1 of a normal presence state, a radar signal 203-1 of an absence state and a radar signal 205-1 of a movement state in each of the set-up environment patterns of FIG. 1A and FIG. 1B. Referring to FIG. 2A, the radar signal 201-1 of the normal presence state in each of the set-up environment patterns is measured while a user is resting or sleeping in a stable presence state.

Referring to a breathing waveform of a lying on side pattern 207 in the radar signal 201-1 of the normal presence state, the radar signal is measured while the sleep testee is lying on his/her side. Thus, the radar signal has a low intensity.

Referring to a breathing waveform of a misdetection object pattern 209 in the radar signal 201-1 of the normal presence state, apnea occurs during sleep of the sleep testee.

As such, it can be seen that a breathing waveform pattern tends to be measured more obviously when the sleep testee is in a stable state.

In contrast, waveforms caused by noises or movements have irregular patterns.

Figure 2B:
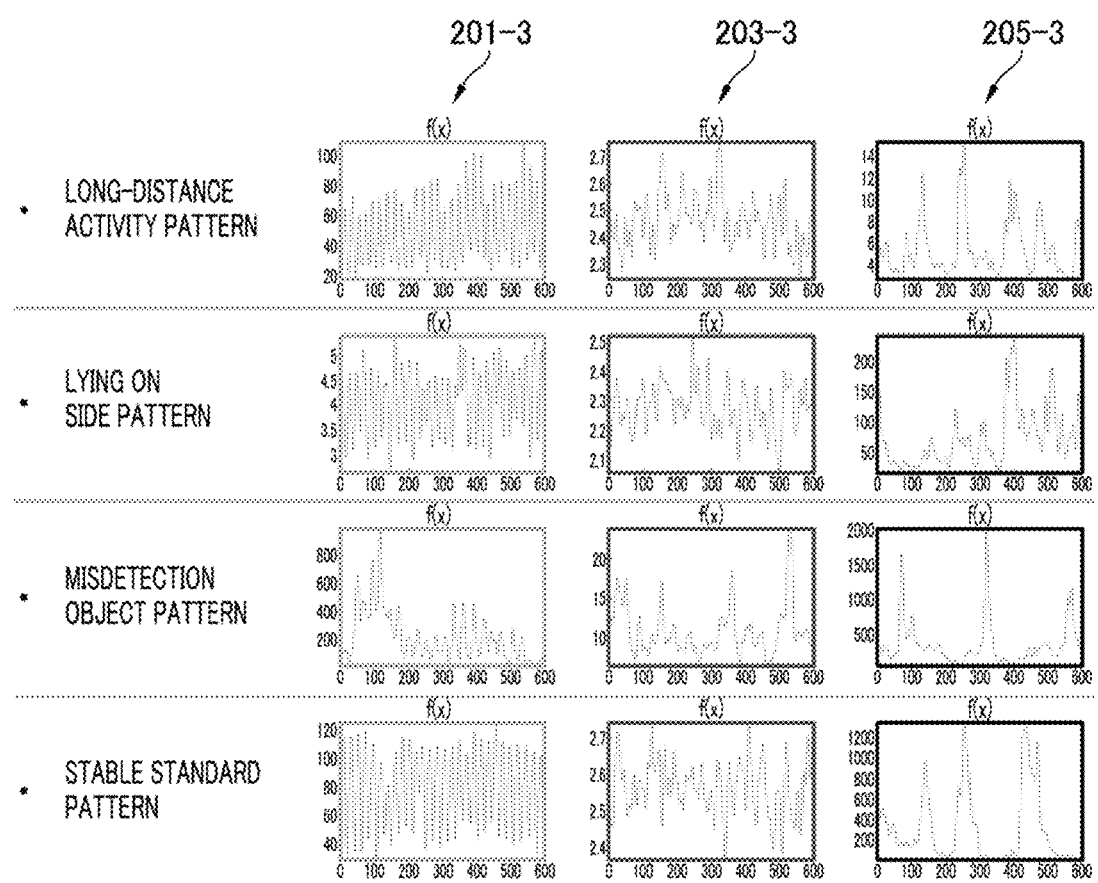

FIG. 2B shows graphs 201-3, 203-3 and 205-3 as results of filtering of the radar signal 201-1 of the normal presence state, the radar signal 203-1 of the absence state and the radar signal 205-1 of the movement state in each of the set-up environment patterns of FIG. 2A. Referring to FIG. 2A and FIG. 2B, a sleep time analysis device of the present disclosure may filter the radar signals 201-1, 203-1 and 205-1 measured for each of the set-up environment patterns according to Equation 1 to distinctly process periodicity in a breathing band.

$$y = 10^{\frac{x}{10}} \qquad \text{[Equation 1]}$$

Herein, the sleep time analysis device may derive the filtered radar signals 201-3, 203-3 and 205-3 by converting the radar signals 201-1, 203-1 and 205-1 in decibel into those in ADC unit to further increase variations in amplitude and then applying a bandpass filter. Herein, the bandpass filter is a $21^{st}$ order finite impulse response (FIR) bandpass filter, and removes all frequency bands except a frequency band of 10 bpm to 30 bpm which is a representative breathing band (i.e., a band including a sign between 10 to 30 per minute which is a normal breathing rate).

The sleep time analysis device may remove DC components by the filtered radar signals 201-3, 203-3 and 205-3 for each of the set-up environment patterns and convert the DC-removed signals to signals that vibrate with respect to 0. Thus, it is possible to suppress a meaningless increase in calculation value by the DC components.

The sleep time analysis device uses autocorrelation in which a signal with more distinct periodicity in the same amplitude range has a change in autocorrelation value. Herein, the autocorrelation is also referred to as serial correlation, and is a kind of convolution product calculated by crossing with a copied signal time-delayed by a time-delay function.

The signals obtained by differentiating the filtered radar signals 201-3, 203-3 and 205-3 can be represented as shown in Equation 2.

$$f'(x) = \lim_{\Delta \to 0} \frac{f(x+\Delta) - f(x)}{(x+\Delta) - x} \qquad \text{[Equation 2]}$$

Equation 2 is differential, and in a discrete domain, Δ becomes 1 and can be derived by real-time processing into Equation 3.

$$f'[x] = f[x] - f[x-1] \qquad \text{[Equation 3]}$$

The sleep time analysis device may calculate an autocorrelation signal using the differentiated signal f'(x). Herein, the autocorrelation signal can be represented as shown in Equation 4.

$$y[n] = f'[n] * f'[n] \qquad \text{[Equation 4]}$$

Figure 2C:
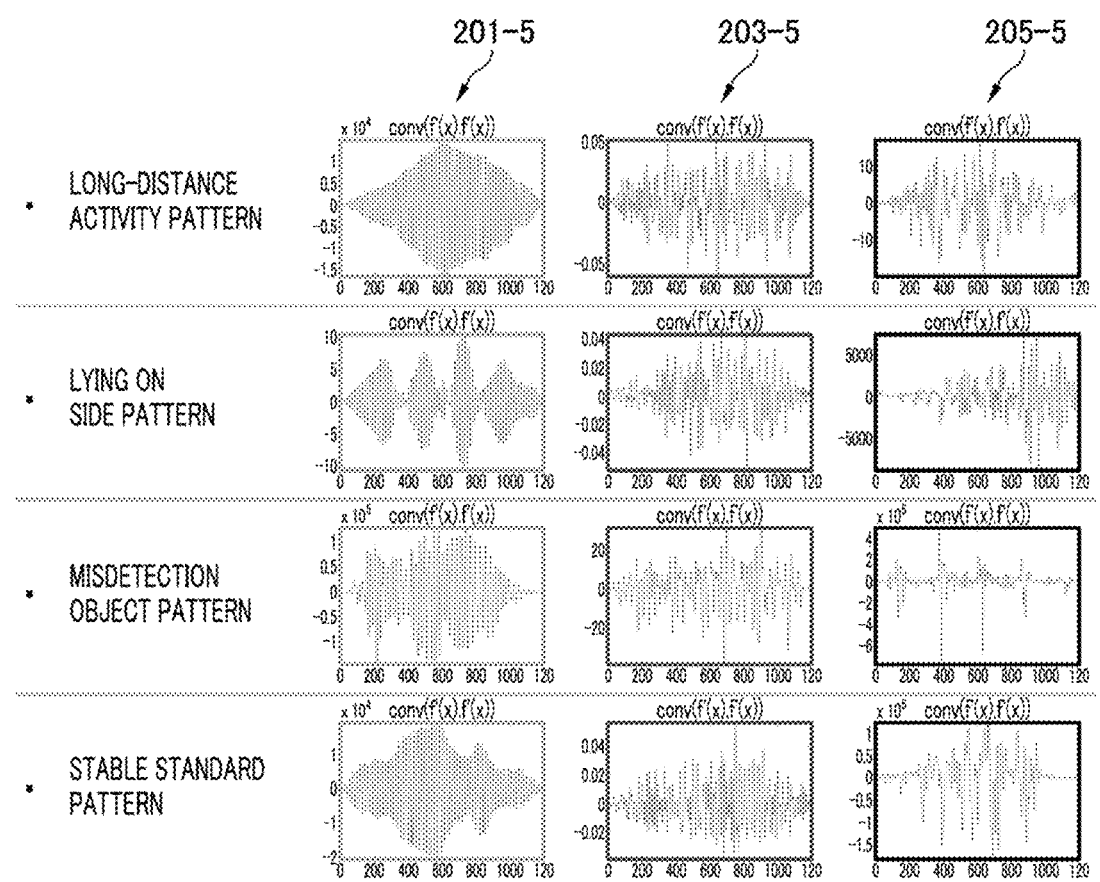

FIG. 2C shows graphs of an autocorrelation signal 201-5 of the normal presence state, an autocorrelation signal 203-5 of the absence state and an autocorrelation signal 205-5 of the movement state in each of the set-up environment patterns.

As the periodicity of an autocorrelation signal becomes more distinct, the widths of the peak and valley become more uniform, and the autocorrelation signal with the distinct periodicity has a narrow width than signals with an indistinct periodicity.

To reflect this phenomenon, the sleep time analysis device may calculate the total sum of absolute values of autocorrelation signals (including all of positive components and negative components) to calculate a periodicity factor. Herein, the periodicity factor is a factor indicating the degree of periodicity in the same amplitude range and can be represented as shown in Equation 5.

$$F_P = \sum_{n=0}^{L} |y[n]| \qquad \text{[Equation 5]}$$

The sleep time analysis device may find the squared summation of autocorrelation signals and calculate a normalization factor using the squared summation. Herein, the normalization factor is a factor for normalizing amplitudes in different ranges and can be represented as shown in Equation 6.

$$F_N = \sum_{x=0}^{L} f'[x]^2 \qquad \text{[Equation 6]}$$

Figure 2D:
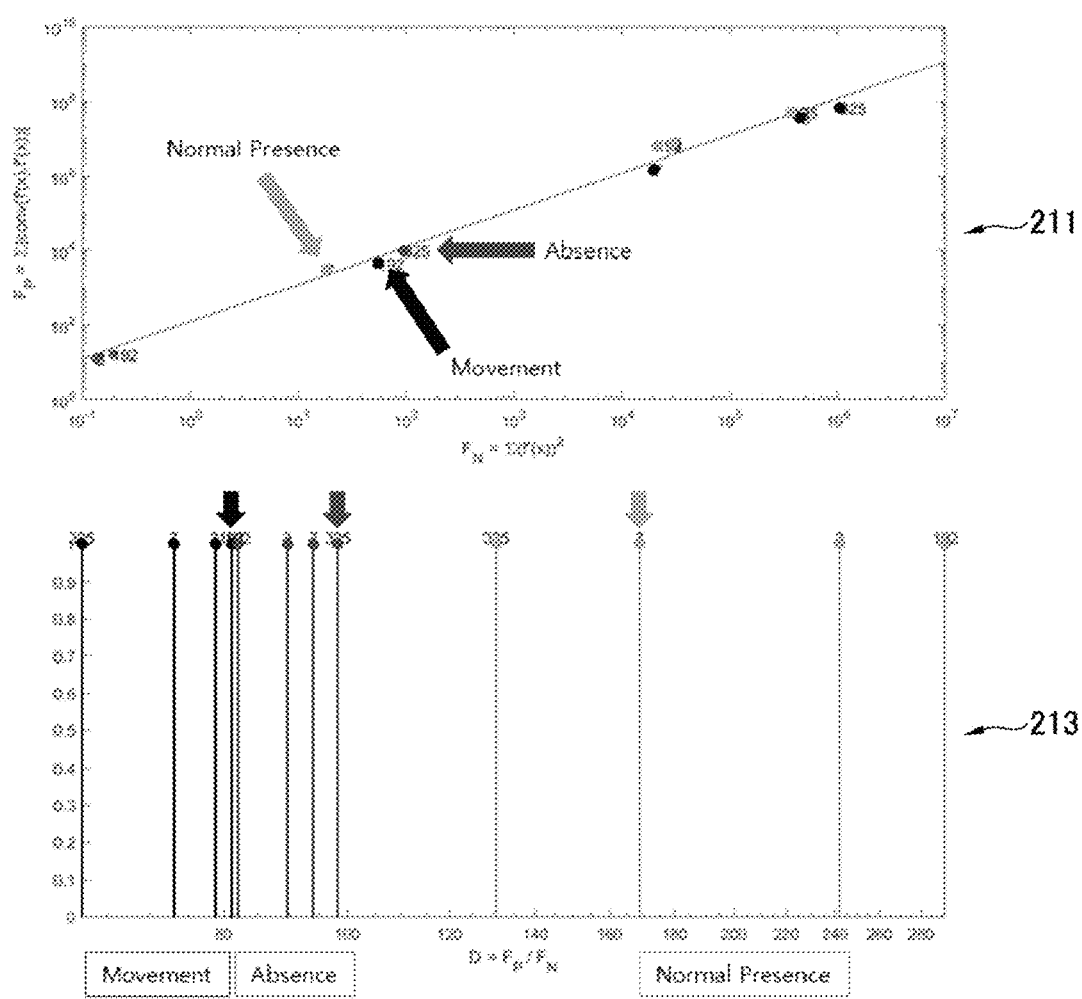

The periodicity factor $F_p$ and the normalization factor $F_N$ can be schematized as a first graph 211 shown in FIG. 2D.

To calculate the general degree of periodicity, the sleep time analysis device may calculate a normalized discriminator D by dividing the periodicity factor by the normalization factor. Herein, the normalized discriminator can be represented as shown in Equation 7.

$$D = \frac{F_P}{F_N} \left( = \frac{\sum_{n=0}^{L} |f'[n] * f'[n]|}{\sum_{x=0}^{L} f'[x]^2} \right) \qquad \text{[Equation 7]}$$

The finally derived normalized discriminator can be schematized as a second graph 213 shown in FIG. 2D.

According to the present disclosure, it is possible to distinguish the presence state by using the normalized discriminator unlike a conventional case where it is impossible to determine whether or not a human subject is present based on the intensities of signals (FIG. 1B).

Referring to the second graph 213 shown in FIG. 2D, it can be seen quantitatively that the periodicity is more distinct in a stable presence state indicated in green.

Hereafter, a state where a subject does not move is equated with a stable presence state to estimate a sleep time of the subject and the stable presence state is detected by using the above-described normalized discriminator according to the present disclosure.

Figure 3:
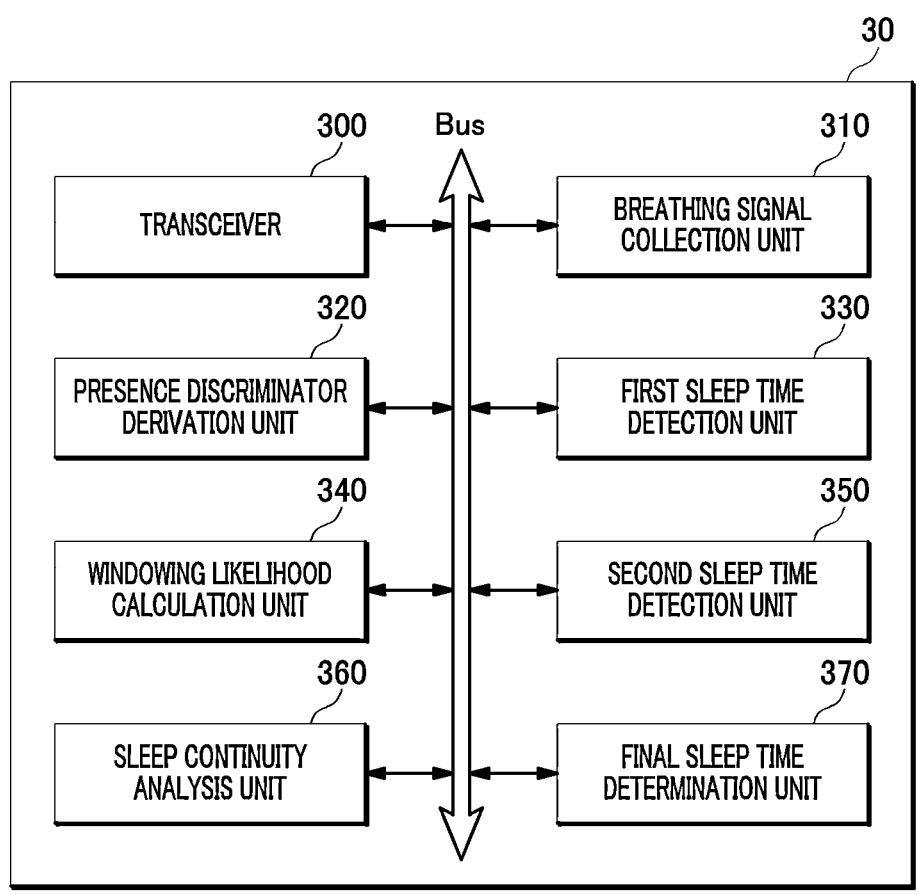
FIG. 3 is a block diagram showing a sleep time analysis device according to an embodiment of the present disclosure.

FIG. 3 is a block diagram showing a sleep time analysis device 30 according to an embodiment of the present disclosure.

Referring to FIG. 3, the, the sleep time analysis device 30 may include a transceiver 300, a breathing signal collection unit 310, a presence discriminator 320, a first sleep time detection unit 330, a windowing likelihood calculation unit 340, a second sleep time detection unit 350, a sleep continuity analysis unit 360 and a final sleep time determination unit 370. However, the sleep time analysis device 30 illustrated in FIG. 3 is just an example of the present disclosure and can be modified in various ways based on the components illustrated in FIG. 3.

Hereafter, description will be made with reference to FIG. 3 together with FIG. 4A to FIG. 4D.

The transceiver 300 may transmit a radar signal toward a subject and receive the radar signal reflected from the subject. For example, the transceiver 300 may transmit a radar signal toward the subject by using a radar and receive the radar signal reflected from the subject through the radar.

Figure 4A:
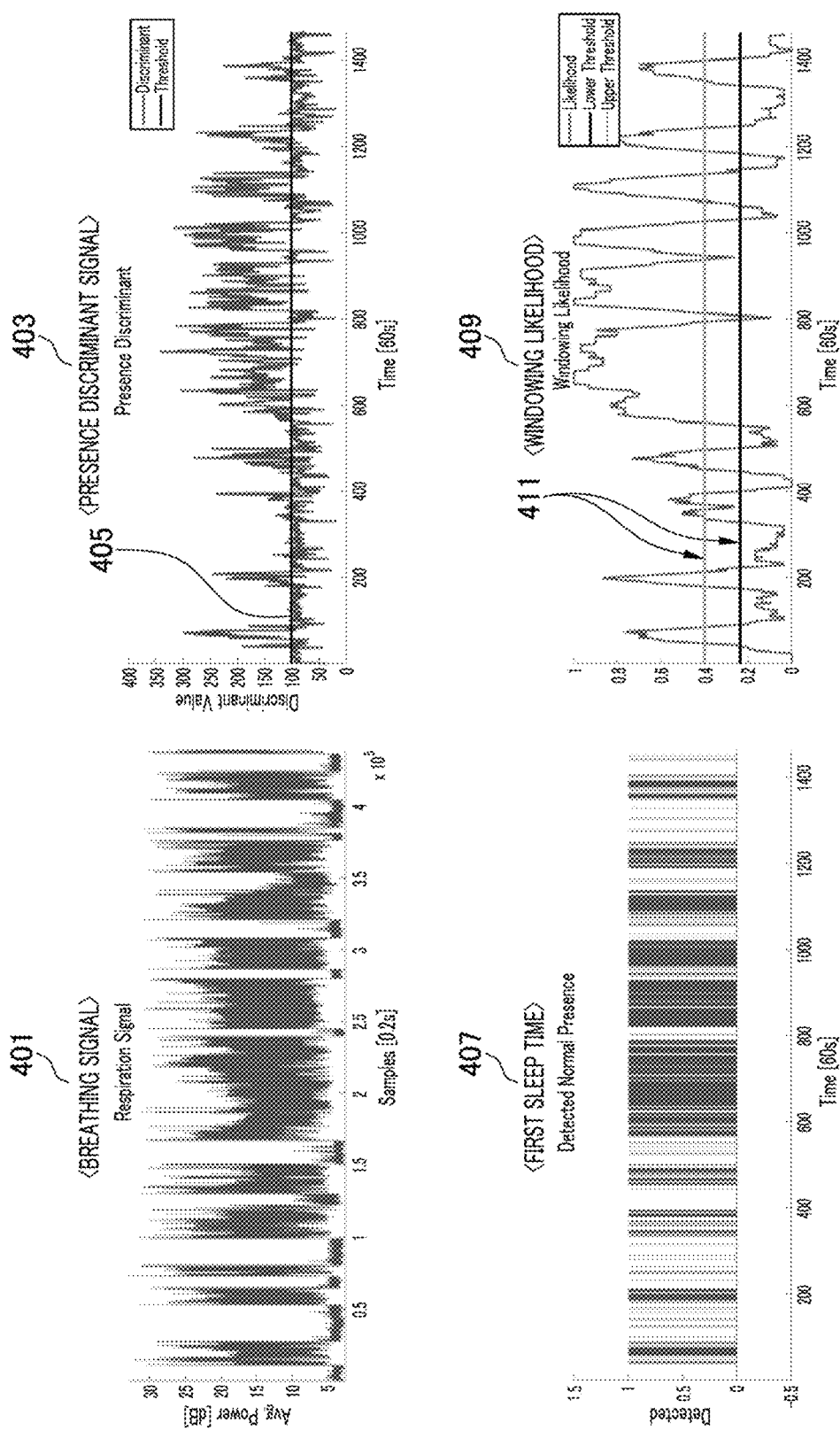
FIG. 4A to FIG. 4D are diagrams provided to explain a method for determining final sleep time according to an embodiment of the present disclosure.

Referring to FIG. 4A, the breathing signal collection unit 310 may collect a breathing signal 401 of the subject based on the radar signal. For example, the breathing signal collection unit 310 may collect breathing signals for 24 hours based on radar signals received from noon on the previous day to noon on the same day.

The presence discriminator 320 may calculate a presence discriminator from the breathing signal 401 by applying moving window settings.

Figure 4B:
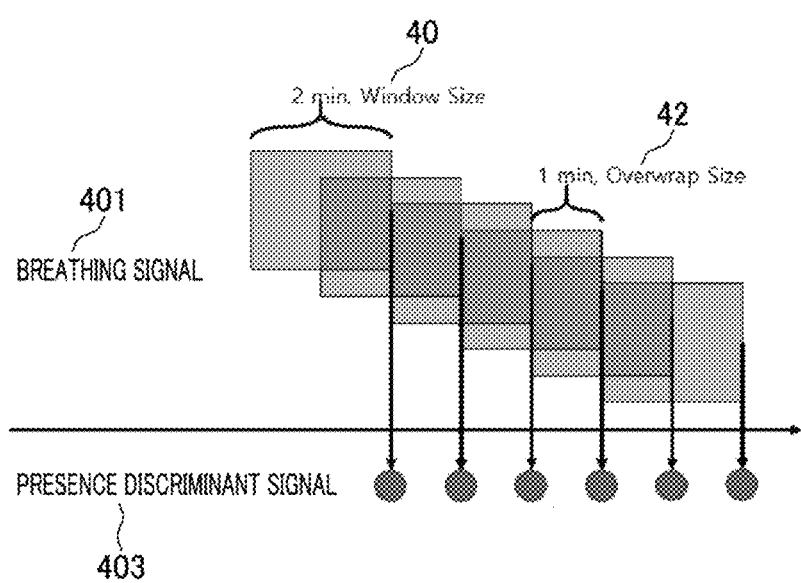

Referring to FIG. 4A and FIG. 4B, the presence discriminator 320 may split the breathing signal 401 into a plurality of split breathing signals based on a window size 40 corresponding to a predetermined first time unit, and may arrange and overlap two or more split breathing signals adjacent to each other among the plurality of split breathing signals at an interval of a predetermined second time unit 42 (overlap size). Herein, the first time unit may include 2 minutes, and the second time unit may include 1 minute.

The presence discriminator 320 may extract a presence discriminant signal 403 for the second time unit from the two or more overlapped split breathing signals, and may derive a presence discriminator 405 from the extracted presence discriminant signal 403 for the second time unit. Herein, the presence discriminator 405 is a single threshold value for determining a presence state without movement, and may numerically split a signal of a stable presence state, a signal of a presence state with movement, and a signal of an absence state.

The first sleep time detection unit 330 may detect a first sleep time 407 of the subject from the breathing signal 401 based on the presence discriminator 405.

The windowing likelihood calculation unit 340 may infer a probability value of the first sleep time 407 based on a predetermined third time unit. Herein, the third time unit may include 30 minutes.

Figure 4C:
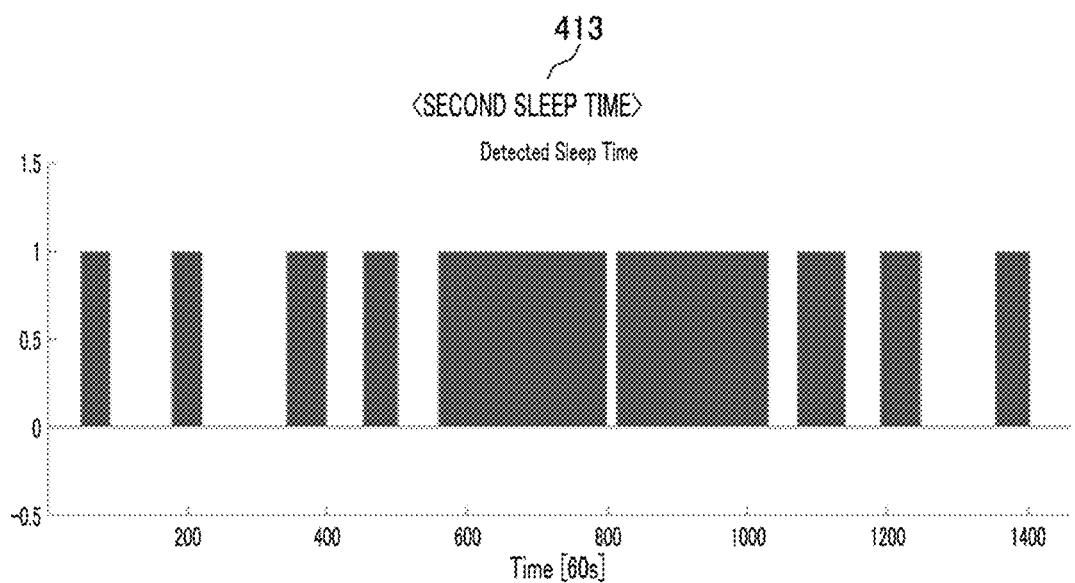
Figure 4C:
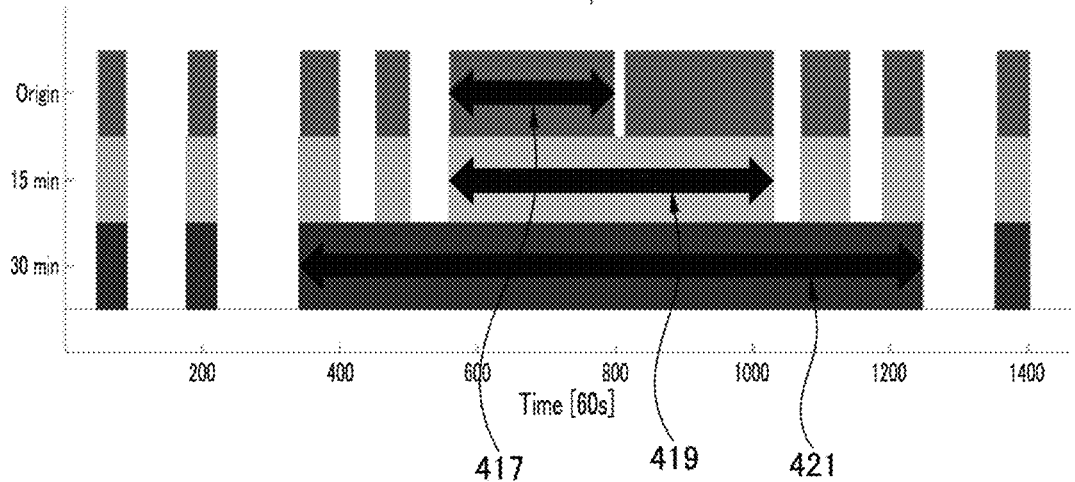

Referring to FIG. 4A and FIG. 4C, the second sleep time detection unit 350 may detect a second sleep time 413 of the subject based on the probability value of the first sleep time 407.

The windowing likelihood calculation unit 340 may calculate a windowing likelihood 409, which indicates a sleep state, from the probability value of the first sleep time 407. Herein, the windowing likelihood 409 may be used to probabilistically estimate the sleep state to a predominant degree of stable presence state.

The graph of the windowing likelihood 409 implies that as the likelihood value increases (i.e., the stable presence state is maintained for 30 minutes), the probability of sleep state increases.

However, the subject may use his/her bed briefly for rest, which may be calculated as being similar to the sleep state. Also, the subject may move during sleep (particularly, during REM sleep), which cannot be determined as a continuous sleep.

Therefore, according to the present disclosure, if movement or absence of the subject is temporary for 30 minutes, it is determined as a continuous sleep by using the likelihood value of the stable presence state.

Although a temporary change in state of the subject is determined as being included in a continuous sleep, the subject may actually go to the bathroom or move for a certain time in response to an external stimulus during sleep. In this case, the present disclosure adopts a double threshold value method to minimize confusion of the presence discriminator. Herein, the double threshold value method is used to suppress frequent changes in results detected around a single threshold value caused by noises when a threshold value is detected from a signal.

The second sleep time detection unit 350 may detect the second sleep time 413 of the subject from the windowing likelihood 409 using a predetermined double threshold value 411. Herein, the double threshold value 411 is used to determine a sleep state depending on how long a temporary stable state is maintained by suppressing changes, and may include a first time threshold value (Upper Threshold) and a second time threshold value (Lower Threshold). The first time threshold value may include, for example, 7 minutes and the second time threshold value may include, for example, 12 minutes.

When a sleep time corresponding to the windowing likelihood 409 is lower than the first time threshold value for the third time unit, the second sleep time detection unit 350 may determine it as an arousal state time. When the sleep time corresponding to the windowing likelihood 409 is higher than the second time threshold value for the third time unit, the second sleep time detection unit 350 may determine it as a sleep state time.

For example, when the time corresponding to a stable presence state is longer than 12 minutes for 30 minutes, the second sleep time detection unit 350 may determine it as a sleep state time, and when it is shorter than 7 minutes for 30 minutes, the second sleep time detection unit 350 may determine it as an arousal state time.

As described above, according to the present disclosure, when the double threshold value 411 is applied based on the windowing likelihood 409, the first sleep time 407 of the subject can be converted into the second sleep time 413 having a density-based continuous form. This is to correct an error by the presence discriminator and an error regarding a temporary change in state.

Meanwhile, sleep patterns differ among individuals. Satisfactory sleep time (i.e., enough sleep time not to cause a problem in everyday life) and intermediate arousal time for terminating sleep differ among individuals.

For example, insomnia is diagnosed based on the degree of discomfort in everyday life caused by sleep rather than objectively measured sleep time. Under these circumstances, sleep continuity requires consideration of the number of various cases for sleep time personally recognized by the subject.

To this end, the sleep continuity analysis unit 360 may analyze various sleep patterns by mathematical morphological analysis. The mathematical morphological analysis includes operations of dilation and erosion and also includes operations of closing (Dilation→Erosion) and opening (Erosion→Dilation) as combinations of the dilation and erosion operations.

Since the dilation and erosion operations are applied both before and after a detection area, the mathematical morphological analysis uses only a half of an interval between removal targets when a function is actually implemented.

Referring to FIG. 4C, the sleep continuity analysis unit 360 may analyze sleep continuity from the second sleep time 413 considering a plurality of predetermined arousal-integrated times.

The sleep continuity analysis unit 360 may analyze sleep continuity from the second sleep time 413 by applying a first arousal-integrated time and a second arousal-integrated time through the closing operation of mathematical morphological analysis. Herein, the first arousal-integrated time may include 30 minutes, and the second arousal-integrated time may include 60 minutes.

When an arousal time included in the second sleep time 413 is shorter than any one of the plurality of arousal-integrated times, the sleep continuity analysis unit 360 may integrate the arousal time into a continuous sleep time.

For example, the sleep continuity analysis unit 360 may determine a basic inferred sleep time 417, which is a continuous sleep time for 5 hours or more in the second sleep time 413, as a first candidate sleep time. Herein, the basic inferred sleep time 417 is 03:59 [21:20-01:18].

The sleep continuity analysis unit 360 may integrate an arousal time of less than 30 minutes among the arousal times included in the second sleep time 413 into the continuous sleep time, and when the continuous sleep time is longer than 5 hours, the sleep continuity analysis unit 360 may determine a 30-minute arousal-integrated time 419 as a second candidate sleep time. Herein, the 30-minute arousal-integrated time 419 may be 07:51 [21:20-05:09].

Also, the sleep continuity analysis unit 360 may integrate an arousal time of less than 60 minutes among the arousal times included in the second sleep time 413 into the continuous sleep time, and when the continuous sleep time is longer than 5 hours, the sleep continuity analysis unit 360 may determine a 60-minute arousal-integrated time 421 as a third candidate sleep time. Herein, the 60-minute arousal-integrated time 421 may be 15:05 [17:42-08:46].

When sleep time is determined, the sleep continuity analysis unit 360 may disregard a sleep time of less than 3 hours, and if sleep fragmentation of 1 hour or more occurs, the sleep continuity analysis unit 360 does not regard it as a continuous sleep. If a continuous sleep for 5 hours or more is detected, the sleep continuity analysis unit 360 may determine it as a candidate sleep time.

Figure 4D:
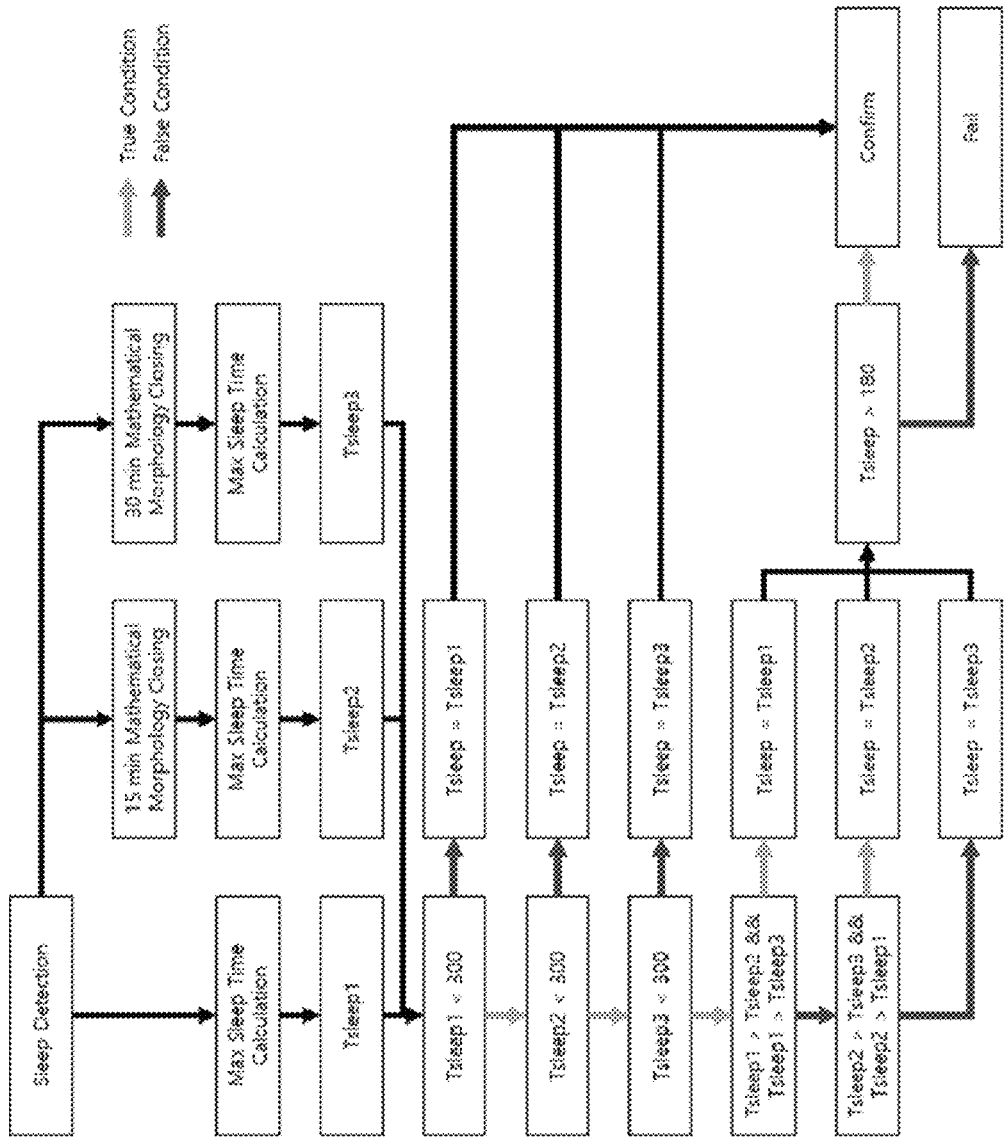

The above-described method for determining sleep time can be schematized as shown in FIG. 4D.

Time set-up parameters, such as 30 minutes and 60 minutes corresponding to the above-described sleep fragmentation-integrated times, and 3 hours and 5 hours corresponding to the minimum sleep times, may be continuously updated in an actual implementation environment. Herein, the time set-up parameters may be regulated depending on, for example, feedback from the subject, regulated according to values set by the subject, regulated based on values derived from data of another subject with high similarity to the subject, regulated according to representative parameters derived from a group with individual variation (e.g., gender, age, body weight, and the like), or regulated according to representative parameters derived from a quasi-group based on survey information of the subject (e.g., disease information, awareness about sleep and insomnia of the subject).

The final sleep time determination unit 370 may determine a final sleep time of the subject based on the second sleep time 413.

The final sleep time determination unit 370 may determine the final sleep time further based on a result of analysis on the sleep continuity.

Referring to FIG. 4C, a sleep continuity analysis result 415 may include the basic inferred sleep time 417 as the first candidate sleep time, the 30-minute arousal-integrated time 419 as the second candidate sleep time and the 60-minute arousal-integrated time 421 as the third candidate sleep time.

The final sleep time determination unit 370 may determine the longest sleep time of the first to third candidate sleep times 417, 419 and 421 as the final sleep time.

Meanwhile, it would be understood by a person with ordinary skill in the art that each of the transceiver 300, the breathing signal collection unit 310, the presence discriminator 320, the first sleep time detection unit 330, the windowing likelihood calculation unit 340, the second sleep time detection unit 350, the sleep continuity analysis unit 360 and the final sleep time determination unit 370 can be implemented separately or in combination with one another.

FIG. 5 is a flowchart showing a method for analyzing sleep time using a radar according to an embodiment of the present disclosure.

Referring to FIG. 5, in a process S501, the sleep time analysis device 30 may transmit a radar signal toward a subject and receive the radar signal reflected from the subject.

In a process S503, the sleep time analysis device 30 may collect a breathing signal of the subject based on the radar signal.

In a process S505, the sleep time analysis device 30 may detect a first sleep time of the subject from the breathing signal based on a presence discriminator.

In a process S507, the sleep time analysis device 30 may detect a second sleep time of the subject based on a probability value of the first sleep time.

In a process S509, the sleep time analysis device 30 may determine a final sleep time of the subject based on the second sleep time.

In the descriptions above, the processes S501 to S509 may be divided into additional processes or combined into fewer processes depending on an embodiment. In addition, some of the processes may be omitted and the sequence of the processes may be changed if necessary.

A computer-readable medium can be any usable medium which can be accessed by the computer and includes all volatile/non-volatile and removable/non-removable media. Further, the computer-readable medium may include all computer storage and communication media. The computer storage medium includes all volatile/non-volatile and removable/non-removable media embodied by a certain method or technology for storing information such as computer-readable instruction code, a data structure, a program module or other data. The communication medium typically includes the computer-readable instruction code, the data structure, the program module, or other data of a modulated data signal such as a carrier wave, or other transmission mechanism, and includes a certain information transmission medium.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A device for analysis of sleep time using a radar, comprising:
   a transceiver configured to transmit a radar signal toward a subject and receive the radar signal reflected from the subject;
   a breathing signal collection unit configured to collect a breathing signal of the subject based on the radar signal;
   a first sleep time detection unit configured to detect a first sleep time during which the subject is in a stable presence state from the breathing signal based on a presence discriminator for distinguishing the stable presence state from an absence state and a movement state for a plurality of set-up environment patterns;
   a windowing likelihood calculation unit configured to calculate a windowing likelihood indicating a degree of time during which the stable presence state is maintained out of a time window based on the first sleep time;
   a second sleep time detection unit configured to detect a second sleep time during which the windowing likelihood is equal to or greater than a likelihood threshold value;
   a sleep continuity analysis unit configured to:
   analyze sleep continuity from the second sleep time considering a plurality of predetermined arousal-integrated times, and
   integrate an arousal time included in the second sleep time into a continuous sleep time when the arousal time is shorter than any one of the plurality of arousal-integrated times; and
   a final sleep time determination unit configured to determine a final sleep time of the subject based on the second sleep time.

2. The device for analysis of sleep time of claim 1, further comprising:
   a presence discriminator derivation unit configured to split the breathing signal into a plurality of split breathing signals based on a window size corresponding to a predetermined first time unit and arrange and overlap two or more split breathing signals adjacent to each other among the plurality of split breathing signals at an interval of a predetermined second time unit,
   wherein the first time unit is longer than the second time unit.

3. The device for analysis of sleep time of claim 2,
   wherein the presence discriminator derivation unit is further configured to derive the presence discriminator from the two or more overlapped split breathing signals.

4. The device for analysis of sleep time of claim 1,
   wherein the time window is a predetermined third time unit, and
   the third time unit is longer than the first time unit.

5. The device for analysis of sleep time of claim 1,
   wherein the second sleep time detection unit is further configured to detect the second sleep time of the subject from the windowing likelihood using a predetermined double threshold value.

6. The device for analysis of sleep time of claim 5,
   wherein the double threshold value includes a first time threshold value and a second time threshold value, and
   the second sleep time detection unit is further configured to determine a sleep time corresponding to the windowing likelihood as an arousal state time when the sleep time is lower than the first time threshold value for the third time unit, and
   the second sleep time detection unit is further configured to determine a sleep time corresponding to the windowing likelihood as a sleep state time when the sleep time is higher than the second time threshold value for the third time unit.

7. The device for analysis of sleep time of claim 1,
   wherein the final sleep time determination unit is further configured to determine the final sleep time further based on a result of analysis on the sleep continuity.

8. A method for analysis of sleep time using a radar that is performed by a sleep time analysis device, comprising:
   transmitting a radar signal toward a subject and receiving the radar signal reflected from the subject;
   collecting a breathing signal of the subject based on the radar signal;
   detecting a first sleep time during which the subject is in a stable presence state from the breathing signal based on a presence discriminator for distinguishing the stable presence state from an absence state and a movement state for a plurality of set-up environment patterns;
   calculating a windowing likelihood indicating a degree of time during which the stable presence state is maintained out of a time window based on the first sleep time;
   detecting a second sleep time when the windowing likelihood is equal to or greater than a likelihood threshold value;
   analyzing sleep continuity from the second sleep time considering a plurality of predetermined arousal-integrated times,
   integrating an arousal time included in the second sleep time into a continuous sleep time when the arousal time is shorter than any one of the plurality of arousal-integrated times; and
   determining a final sleep time of the subject based on the second sleep time.

9. The method for analysis of sleep time of claim 8, further comprising:
   splitting the breathing signal into a plurality of split breathing signals based on a window size corresponding to a predetermined first time unit; and
   arranging and overlapping two or more split breathing signals adjacent to each other among the plurality of split breathing signals at an interval of a predetermined second time unit,
   wherein the first time unit is longer than the second time unit.

10. The method for analysis of sleep time of claim 9, further comprising:
- deriving a presence discriminator from the two or more overlapped split breathing signals.

11. The method for analysis of sleep time of claim 8, wherein the time window is a predetermined third time unit,
wherein the third time unit is longer than the first time unit.

12. The method for analysis of sleep time of claim 11, wherein the detecting a second sleep time of the subject includes:
- detecting the second sleep time of the subject from the windowing likelihood using a predetermined double threshold value.

13. The method for analysis of sleep time of claim 12, wherein the double threshold value includes a first time threshold value and a second time threshold value, and the method further includes:
- determining a sleep time corresponding to the windowing likelihood as an arousal state time when the sleep time is lower than the first time threshold value for the third time unit, and
- determining a sleep time corresponding to the windowing likelihood as a sleep state time when the sleep time is higher than the second time threshold value for the third time unit.

14. The method for analysis of sleep time of claim 8, wherein the determining a final sleep time of the subject includes:
determining the final sleep time further based on a result of analysis on the sleep continuity.

\* \* \* \* \*